United States Patent
Hu et al.

(10) Patent No.: US 8,956,659 B2
(45) Date of Patent: Feb. 17, 2015

(54) FULVESTRANT NANOSPHERE/MICROSPHERE AND PREPARATIVE METHOD AND USE THEREOF

(71) Applicant: Xi'an Libang Pharmaceutical Technology Co., Ltd., Xi'an (CN)

(72) Inventors: Renle Hu, Xi'an (CN); Jiucheng Wang, Xi'an (CN); Yaqi Jiao, Xi'an (CN); Hua Liang, Xi'an (CN); Duohao Ding, Xi'an (CN)

(73) Assignee: Xi'an Libang Pharmaceutical Technology Co., Ltd., Xi'an (CN)

( * ) Notice: Subject to any disclaimer, the term of this patent is extended or adjusted under 35 U.S.C. 154(b) by 0 days.

(21) Appl. No.: 14/056,049

(22) Filed: Oct. 17, 2013

(65) Prior Publication Data
US 2014/0042654 A1 Feb. 13, 2014

Related U.S. Application Data

(62) Division of application No. 13/255,054, filed as application No. PCT/CN2009/000990 on Aug. 31, 2009, now Pat. No. 8,586,092.

(51) Int. Cl.
*A61K 9/14* (2006.01)
*A61K 47/34* (2006.01)
*A61K 9/00* (2006.01)
(Continued)

(52) U.S. Cl.
CPC ............... *A61K 47/34* (2013.01); *A61K 9/0019* (2013.01); *A61K 9/0024* (2013.01); *A61K 9/1641* (2013.01); *A61K 9/1647* (2013.01); *A61K 9/5031* (2013.01); *A61K 9/5089* (2013.01); *A61K 31/565* (2013.01); *A61K 9/14* (2013.01)
USPC .......................................................... 424/489

(58) Field of Classification Search
None
See application file for complete search history.

(56) References Cited

U.S. PATENT DOCUMENTS

| 8,187,640 B2 | 5/2012 | Dunn |
| 2011/0038856 A1* | 2/2011 | Drachman et al. ......... 424/133.1 |

FOREIGN PATENT DOCUMENTS

| CN | 1412220 A | 4/2003 |
| CN | 101108168 A | 1/2008 |
| WO | 2011022861 A1 | 3/2011 |

OTHER PUBLICATIONS

Wang et al. Preparation and Release characteristics in vitro of tacrolimus nanosphreres, Abstract, Journal of Applied Polymer Science, VOl 98, 2116-2122 (2005).*

(Continued)

*Primary Examiner* — Robert A Wax
*Assistant Examiner* — Melissa Mercier
(74) *Attorney, Agent, or Firm* — Chainey P. Singleton; Edwin S. Flores; Chalker Flores, LLP

(57) ABSTRACT

Fulvestrant nanosphere/microsphere and preparation method and use thereof are provided in the present invention. The carrier material of the fulvestrant nanosphere/microsphere is methoxy ended polyethylene glycol-polylactic acid block copolymer. The nanosphere/microsphere is prepared by solvent-nonsolvent method, in-liquid drying method and/or spray drying method, and has the features of high drug loading and high encapsulation efficiency, controllable release of medicine and no irritant to application site or blood vessel. The fulvestrant nanosphere/microsphere can be used to treat metastatic advanced breast cancer in post-menopausal woman.

20 Claims, 4 Drawing Sheets

(51) Int. Cl.
*A61K 9/16* (2006.01)
*A61K 9/50* (2006.01)
*A61K 31/565* (2006.01)

(56) References Cited

OTHER PUBLICATIONS

Sasatsu, M., "Preparation and biodisposition of methoxypolyethylene glycol amine-poly(DL-lacic acid) copolymer nanoparticles loaded with pyrene-ended poly(DL-lactic acid)," International Journal of Pharmaceutics (2008) 271-277.

International Search Report (ISA/CN) PCT/CN2009/000990 Dated May 24, 2010.

Deng, et al., "Methoxy Poly(ethlene glycol)-b-Poly(L-lactic acid) Copolymer Nanoparticles as Delivery Vehicles for Paclitaxel," Journal of Applied Polymer Science (Feb. 10, 2005) vol. 98, pp. 2116-2122.

Wang, et al., "Preparations and release characteristics in vitro of tacrolimus nanospheres," Chin J. Mod Drug Appl (Jul. 2008) vol. 2 No. 14, pp. 21-23.

* cited by examiner

FULVESTRANT NANOSPHERE/MICROSPHERE AND PREPARATIVE METHOD AND USE THEREOF

CROSS-REFERENCE TO RELATED APPLICATIONS

The present application is a divisional application of U.S. application Ser. No. 13/255,054 titled FULVESTRANT NANOSPHERE/MICROSPHERE AND PREPARATIVE METHOD AND USE THEREOF, which is filed on Sep. 6, 2011. The present application claims the priority of PCT/CN2009/000990, which is filed on Aug. 31, 2009.

TECHNICAL FIELD OF THE INVENTION

The present invention relates to the field of medical technology. Specifically, the present invention relates to a kind of fulvestrant nanosphere or microsphere, and preparation method and use of the fulvestrant nanosphere or microsphere formulation.

BACKGROUND OF THE INVENTION

The World Health Organization has ranked the breast cancer as the "leading killer" threatening to female health, and there are about 1 million female die of breast cancer each year in the world. The clinical data shows that about 80% of adult females have some degree of breast cancer in China, the morbidity rate of which is still increasing and now it has increased from 170 per million five years ago to 520 per million last year, which is more than three times higher. In recent 20 years, the morbidity rate of the breast cancer has increased around 180% in shanghai. Meanwhile, with the increasing cancer lesions, the number of women who die of breast cancer is up to 0.2 million every year, leading to disastrous panic to female health.

Now, drugs for the treatment of breast cancer mainly include: (1) chemotherapeutic drugs: such as capecitabine, docetaxel, 5-fluorouracil, doxorubicin, cyclophosphamide, paclitaxel, vinorelbine, etc.; (2) I trastuzumab and other signal transduction inhibitors: trastuzumab, clodronate, pamidronate, ibandronate, and zoledronate etc.; (3) endocrine inhibitor: tamoxifen, anastrozole, letrozole, exemestane, buserelin or goserelin, fulvestrant, and the like. Among them, most chemotherapeutic drugs have the shortage of high toxic and side effect, low improved survival, increased long term toxicity, and high cost of combined chemotherapy, etc.; I trastuzumab and other signal transduction inhibitors are most used as the adjuvant therapy of chemotherapeutic drugs. As compared to the chemotherapeutic drugs, new progress in endocrine inhibitor therapy has more important significance: tamoxifen is almost the gold standard for the endocrine therapy of breast cancer in recent 30 years, and anastrozole has potential prevention effect on breast cancer. Fulvestrant is an anti-estrogen drug. Unlike tamoxifen, fulvestrant is able to down regulate the estrogen receptor without partial agonist activity. Fulvestrant has clinical therapeutic effect in patients failed in treatment with tamoxifen. Therefore, among many drugs for treating breast cancer, fulvestrant is the only anti-estrogen agent that may be widely used in clinical treatment after the failure of tamoxifen, which has initiated a new way of treating hormone-sensitive breast cancer.

The chemical name of fulvestrant is 7-alpha-[9-(4,4,5,5,5-pentafluoropentylsulphinyl)nonyl]estra-1,3,5-(10)-triene-3,17-beta-diol. Fulvestrant is a white or off-white powder, insoluble in water with a relative molecular weight of 606.77.

Fulvestrant is a new estrogen receptor antagonist-anti-breast cancer drugs of estrogen receptor down regulators. Currently, the main method for treatment of breast cancer is to decrease the concentration of estrogen due to estrogen receptors (ER) are found in many patients with breast cancer and the growth of tumor is stimulated by estrogen. Fulvestrant may competitively combine with estrogen receptor with the affinity similar to that of estradiol; fulvestrant may also block the receptor, inhibit its combination with the estrogen, and stimulate the receptor to have morphological changes, decrease the concentration of ER to damage the tumor cell, such effect through ER path is related to the decreasing of the cell proliferation makers, Ki67. Fulvestrant can down regulate ER protein in human breast cancer cell, and the ER is down regulated within tumor cell to minimize the growth of tumor. Because fulvestrant do not change the status of the existing tumor ER, and do not affect on the production of new ER, the tumor is continued to be "programmed" as ER positive, so that fulvestrant can continuously have a therapeutic effect. Animal experiments found that fulvestrant had no estrogen effect or anti estrogen effect of tamoxifen or the partial agonist activity on the endometrium, so its adverse effect is less than that of tamoxifen, particularly the latter has the risk of increasing the incidence rate of endometrial carcinoma.

Fulvestrant is insoluble in water causing poor oral bioavailability and being eliminated immediately after the intravenous injection. Accordingly, oral preparation and common water solution for injection are not applicable to this drug. Fulvestrant shows, along with other steroidal based compounds, certain physical properties which make formulation of these compounds difficult. Fulvestrant is a particularly lipophilic molecule, even when compared with other steroidal compounds, and its aqueous solubility is extremely low at around 10 ng/ml.

Currently there are a number of sustained release injectable steroidal formulations which have been commercialized. Commonly, these formulations use oil as a solvent, and wherein additional excipients may be present. For example, Chinese patent application CN1553815A disclosed a pharmaceutical formulation for the intramuscular administration of fulvestrant on Dec. 8, 2004, that is an oil based injection formulation of fulvestrant of AstraZeneca UK Ltd. in sweden, which is approved by FDA on April 2002 with the trade name of Faslodex®. The solvent system of the product consists of ethanol, benzyl alcohol, benzyl benzoate, and castor oil, adapted for breech intramuscular injection, in which the content of ethanol is 10%~20%, the content of benzyl alcohol is 10%~20%, the content of benzyl benzoate is 15%~50%, and the content of castor oil is 5%~60%. All these chemical ingredients have strong irritation, and many of their adverse reactions have reported: LD50 of ethanol subcutaneous injection into mouse is 8.285 g/kg, and a pain is felt when the concentration of intramuscular injection is higher than 10%. Benzyl alcohol is a colorless-transparent oily liquid with weak fragrant smell and pungent taste, the LD50 of which orally administered to rat is 1.23 g/kg. Benzyl benzoate a colorless-transparent oily liquid with faint fragrant smell, tongue contact causes a feeling of intense burning, and the LD50 of which orally administered to rat is 0.5 g/kg. Castor oil is a clear, colorless or yellowish, viscid and oily liquid with slight odor, tasteless in the first taste but later having pungent taste, and clinically is mainly used for irritant laxatives. On Dec. 20, 2004, Chinese Medicine Information News published the report titled as "Benzyl alcohol should be used cautiously for eradicating 'frog foot disease' on "Pharmacovigilance" column, which reported that 311 children were suffered from gluteal muscle contracture as a result of the use of benzyl alcohol as a solvent of penicillin in Zhongying township, Hefeng County of Hubei Province. On Nov. 1, 2005, Chinese Medicine Information News published the report titled as "Concerning the adverse effects caused by pharmaceutical adjuvant" on "Hot Concern" column, which indicated that ethanol was applied to many injections of the insoluble drug as a solvent, and intramuscular or subcutaneous injection of them would cause great irritation. At first, a burning sensation is caused at the injection site, severe pain, local anesthesia occurs afterwards. It can cause neurodegenerative damage when being injected near nerve carelessly. The article also indicated that, as a solvent of drug, preservatives (0.5%~1.0%), and topical analgesics (1%~4%), the adverse reaction of benzyl alcohol comprises hemolysis, hypotension, localized stimulus and the like. Benzyl alcohol can be bound to the surface of the red cell membrane, leading to hemolysis. It is also reported that one patient developed respiratory depression and fast hemolysis after receiving high dose of etoposide containing benzyl alcohol for treating non-hodgkin's lymphoma. Another report said that the solvent benzyl alcohol in amiodarone injection has activity of blood vessel, producing hypotension. Benzyl alcohol is also the main reason of causing gluteal muscle contracture. On Jun. 10, 2005, the State Food and Drug Administration issued "Notice on Strengthening Management of Benzyl Alcohol Injection" (No. [2005] 263 of the State Food and Drug Administration) ordered that benzyl alcohol is forbidden to use for intramuscular injection in children.

Thus, fulvestrant injection (Faslodex®) consists of the above non-aqueous chemical solvent with strong irritation which may damage the injection site. There are more than 10% of patients developing pain at the injection site in their clinical trial and the damage degree is strengthened with the increase of the dosage. After injection of Faslodex®, the non-aqueous chemical solvent is absorbed into the human muscle tissue, and then the drug is precipitated into the muscle tissue, followed by slow absorption. The release process of the drug is uncontrollable because of the rapid absorption of the non-aqueous chemical solvent by the muscle tissue, it also leads to the uncontrollability of the absorption rate of drug. More importantly, it has to use the fulvestrant oil injection with higher concentration and more non-aqueous solvent to extent the efficacy of the drug, which brings greater damage to the injection site when the fulvestrant oil injection is used for treatment in clinical in order to achieve longer time of the drug action.

Therefore, for the promising drug fulvestrant, a new formulation with no irritates to the administration site or vessel, low side effect and available for intravenous injection is needed to be developed.

SUMMARY OF THE INVENTION

Polyethylene glycol-polylactic acid block copolymer is an appropriate carrier material for preparing nanosphere or microsphere, due to it is composed of hydrophilic fragment polyethylene glycol and lipophilic fragment polylactic acid, has good thermoplasticity and thermosetting, also has biodegradability and biocompatibility, and has no irritate to the injection site and blood vessel. The U.S. Food and Drug Administration (FDA) has approved such material to be used for the drug controlled and sustained release carriers. Using such material as the drug carriers may avoid the oily solvents causing pain and inflammation to the injection site. Meanwhile, the drug carrier release the drug with the degradation of the carrier material in vivo, and the release rate of the drug can be regulated by regulating the molecular weight of the block and the HLB value of the carrier material.

The inventor surprisingly found in the research work that fulvestrant nanosphere or microsphere prepared by using the methoxy ended polyethylene glycol-polylactic acid block copolymer as carrier material can essentially solve the problems of the existing fulvestrant oil injection products that cause damage to the injection site and have uncontrolled drug release, absorption. The nanosphere or microsphere can be administered for intravenous injection, solving the problem of the drug can not be administered for intravenous injection.

Therefore, one object of the present invention is to provide a kind of fulvestrant nanosphere or microsphere that has higher drug loading and entrapment rate and controlled drug release rate but without irritation to the administration site or blood vessel; another object of the present invention is to provide a method for preparing the above fulvestrant nanosphere or microsphere; further object of the present invention is to provide the use of the above fulvestrant nanosphere or microsphere.

Aiming at the above inventive object, the technical solutions of the present invention are as follows:

In one aspect, the present invention provides a drug carrier of fulvestrant nanosphere or microsphere, the carrier includes the biodegradable methoxy ended polyethylene glycol-polylactic acid block copolymer, described as the formula (I) of:

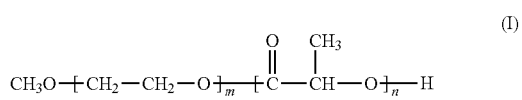

wherein: m=4~454, n=4~2778.

According to the above mentioned drug carrier of fulvestrant, wherein the methoxy ended polyethylene glycol-polylactic acid block copolymer is composed of hydrophilic fragment polyethylene glycol and lipophilic fragment polylactic acid with the HLB value of 0.01~19.84.

According to the above mentioned drug carrier of fulvestrant, wherein the encapsulated drug is 7-alpha-[9(4,4,5,5,5-pentafluoropentylsulphinyl)nonyl] estra-1,3,5-(10)-triene-3, 17-beta-diol, the International Nonproprietary Name of which is fulvestrant that is used herein. When it comes to fulvestrant, the pharmaceutically acceptable salt thereof or any possible solvate thereof should be included, such as the 17 hydroxyl in the structural formula of fulvestrant can be substituted with acetoxy or benzoyloxy.

In another aspect, the present invention provides a kind of fulvestrant nanosphere or microsphere comprising fulvestrant or pharmaceutically acceptable salt thereof or any possible solvate thereof and a carrier material of a methoxy ended polyethylene glycol-polylactic acid block copolymer.

Preferably, the fulvestrant nanosphere or microsphere comprises 0.01%~50% weight of fulvestrant or pharmaceutically acceptable salt thereof or any possible solvate thereof based on the amount of fulvestrant, preferably 5%~50% weight, more preferably 10%~30% weight, and most preferably 20%~30% weight. I.e. the drug loading rate of the fulvestrant nanosphere or microsphere is 0.01%~50% weight, preferably 5%~50% weight, more preferably 10%~30% weight, and most preferably 20%~30% weight.

Preferably, in the fulvestrant nanosphere or microsphere, the methoxy ended polyethylene glycol-polylactic acid block copolymer is composed of hydrophilic fragment polyethylene glycol and lipophilic fragment polylactic acid; preferably, the structural formula of the methoxy ended polyethylene glycol-polylactic acid block copolymer is

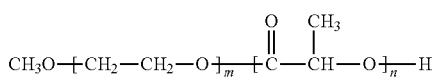

wherein: m=4~454, n=4~2778; preferably m=11~227, n=70~2083, more preferably m=22~113, n=139~1111. The value of hydrophile-lipophile balance (HLB) of the methoxy ended polyethylene glycol-polylactic acid block copolymer is 0.01~19.84; preferably the HLB is 0.4~12.0, more preferably the HLB is 1.47~15.0.

Preferably, the particle size of the fulvestrant nanosphere is 0.1 μm~1 μm, preferably 0.3~0.8 μm; the particle size of the fulvestrant microsphere is 10 μm~1 mm, preferably 10 μm~500 μm.

In further aspect, the present invention provides a method for preparing the above mentioned fulvestrant nanosphere or microsphere, the method includes solvent-nonsolvent method, in-liquid drying method and spray drying method.

In one preferred embodiment, the solvent-nonsolvent method includes the steps of:
a. dispersing or dissolving the fulvestrant in the solvent system containing the dissolved carrier material described above;
b. added into nonsolvent system to form nanosphere or microsphere;
c. solidifying, collecting, washing and drying;
preferably, the solvent of the carrier material is one or more of dichloromethane, trichloromethane, methylhydrofuran, ethanol, and ethyl acetate;
preferably, the concentration of the carrier material in the solvent system is 0.1%~50% (g/ml);
preferably, the concentration of the fulvestrant in the solvent system which contains dissolved carrier material is 0.01%~80% (g/ml);
preferably, the nonsolvent system is ether, petroleum ether, n-hexane, cyclohexane, acetone;
preferably, the volume ratio of the solvent system to the nonsolvent system is 10:1~1:10; and/or
preferably, adding one or more of polyisobutyl ester, polyethylene, and butyl rubber into the nonsolvent system as antisticking agent; more preferably, the mass ratio of the antisticking agent to the carrier material is 0:10~2:10.

In another preferred embodiment, the in-liquid drying method includes the steps of:
a. dissolving the fulvestrant and the above mentioned carrier material in the organic solvent to make an oil phase;
b. adding the oil phase in the aqueous phase and emulsifying to get the oil-in-water O/W type emulsion;
c. stirring and heating up the O/W type emulsion to completely volatilize the organic solvent in the 0/W type emulsion;
d. filtering, washing, collecting and drying;
preferably, the solvent of the carrier material is one or more of dichloromethane, trichloromethane, methylhydrofuran, ethanol, and ethyl acetate;
preferably, the mass ratio of the fulvestrant to the carrier material is 1:50-1:3;
preferable concentration of the carrier material in the oil phase is 1%~50% (g/ml);
preferably, the aqueous phase is one or more mixed solution of surfactant solution, mono- or polysaccharides solution, polyol solution, cellulose solution, and colloid solution, the concentration of the solute in the aqueous phase is 0.01%~50% (g/ml), and the pH value of aqueous phase is in the range of 3.0~10.5;
preferably, the pH adjusting agent used in the aqueous phase is selected from the group consisting of inorganic acid, organic acid, inorganic base, organic base and buffer salt; and/or
preferably, the volume ratio of the oil phase to the aqueous phase is 1:300~1:5.

In further preferred embodiment, the spray drying method includes the steps of:
a. dissolving or dispersing the fulvestrant in the solvent system containing the dissolved carrier material as described above;
b. spraying into the drying tower of spray drying equipments in the form of spray, and drying, isolating, collecting;
preferably, the solvent of the carrier material is one or more of dichloromethane, trichloromethane, methylhydrofuran, ethanol, and ethyl acetate;
preferably, the concentration of the carrier material in the solvent system is 0.1%~50% (g/ml);
preferably, the concentration of the dissolved or dispersed fulvestrant in the solvent system of the carrier material is 0.01%~50% (g/ml);
preferably, the inlet air temperature of the drying tower is 30~80;
preferably, the carrier material further comprises plasticizer; more preferably, the plasticizer is one or more of dimethyl benzoate, diethyl benzoate, dibutyl benzoate, dibutyl sebacate, tributyl citrate, acetyl tributyl citrate, and glyceryl triacetate;
further preferably, the mass percent of the plasticizer to the carrier material is 0%~50%; and/or
preferably, the solvent system further comprises antisticking agent, the antisticking agent is one or more of cholesterol, glycerol monostearate, talc powder, silica gel, and magnesium stearate, the mass percent of the antisticking agent to the carrier material is 0%~100%.

In another aspect, the present invention provides the use of the above mentioned fulvestrant nanosphere or microsphere in the preparation of the drugs for treating breast cancer; preferably, the breast cancer is advanced breast cancer, more preferably, the breast cancer is the metastatic advanced breast cancer in post-menopausal woman with ineffective, progressed or hormone receptor-positive after treating with antiestrogen therapy. Furthermore, the present invention also provides a pharmaceutical composition for treating breast cancer, comprising the above mentioned fulvestrant nanosphere or microsphere.

In still another aspect, the present invention also provides the use of the above mentioned fulvestrant nanosphere or microsphere and the above mentioned pharmaceutical composition for treating breast cancer; preferably, the breast cancer is advanced breast cancer, more preferably, the breast cancer is the metastatic advanced breast cancer in post-menopausal woman with ineffective, progressed or hormone receptor-positive after treating with antiestrogen therapy.

In yet another aspect, the present invention provides a method of treating breast cancer, especially the metastatic advanced breast cancer in post-menopausal woman with ineffective, progressed or hormone receptor-positive after treating with antiestrogen therapy, comprising administering to the patient in need thereof a pharmaceutically acceptable effective amount of the above mentioned fulvestrant nanosphere or microsphere, or the above mentioned pharmaceutical composition, and the fulvestrant nanosphere or microsphere or the pharmaceutical composition can be administered every 1 to 3 months; preferably, the administration route is subcutaneous or intravenous injection.

Thus, it can be seen that the present invention provides a kind of fulvestrant nanosphere or microsphere, wherein the capsulated active substance is fulvestrant, and the carrier material of which is methoxy ended polyethylene glycol-polylactic acid block copolymer. The fulvestrant nanosphere or microsphere and the pharmaceutical composition thereof avoid the damages such as irritation to injection site caused by the non-aqueous solvent in clinical use. The fulvestrant nanosphere or microsphere or the pharmaceutical composition thereof can be subcutaneously or intravenously injected. The fulvestrant is slowly released with the degradation of the carrier material after injection, and the release rate can be regulated by regulating the molecular weight of the hydrophilic fragment polyethylene glycol and the lipophilic fragment polylactic acid in the carrier material, that is, the release and absorption rate of the drug can be regulated by regulating the HLB value of methoxy ended polyethylene glycol-polylactic acid block copolymer of the carrier material to fulfill different clinical needs. The fulvestrant nanosphere or microsphere or the pharmaceutical composition thereof can be used for the treatment of the metastatic advanced breast cancer in post-menopausal woman with ineffective, progressed or hormone receptor-positive after treating with antiestrogen therapy.

In the fulvestrant nanosphere or microsphere and the pharmaceutical composition thereof provided in the present invention, the inventor has surprisingly found that the most suitable drug carrier for fulvestrant nanosphere or microsphere is the methoxy ended polyethylene glycol-polylactic acid block copolymer which has stronger biocompatibility on human body. Using such carrier, the nanosphere or microsphere formulation possesses desired drug release and pharmacokinetic performance, it avoids the use of a large number of irritant non-aqueous chemical solvent, such that the fulvestrant nanosphere or microsphere and composition thereof has no irritant damage to the human blood vessel and skin tissue, and release fulvestrant with the degradation of the carrier material after injection with stable and controllable release rate. The fulvestrant nanosphere or microsphere provided in the present invention can also be used for intravenous injection, which has changed the situation that such drug can not be administered intravenously, and has provided a new administration route for clinical use. Thus, if the fulvestrant nanosphere or microsphere and the composition thereof provided by the present invention can be developed into commodity, they must take the place of their oil injective formulation in clinical, and also open up a new prospect for fulvestrant in clinical use, which will have wide application prospect.

DETAILED DESCRIPTION OF THE INVENTION

Figure 1:
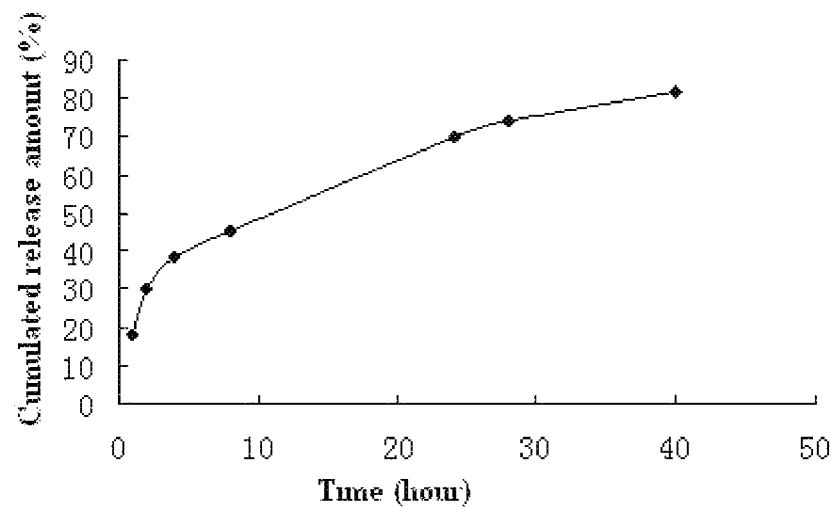
FIG. 1 is a release curve of fulvestrant microsphere sample 1 in vitro.

The present invention will be further illustrated in detail with reference to the following examples or embodiments, it should be understood that the following examples only illustrate and explain the present invention and do not limit the scope of the present invention.

It should be understood that for the method, step, appliance, instrument, material and the like which is referred to but not described in detail, it can be obtained by those of ordinary skill in the art through using the well known corresponding method, step, appliance, instrument, material and the like or according to the conventional knowledge and technique in the art.

Unless otherwise indicated, the specific chromatographic conditions of HPLC method used in each of the following examples are as follows: octadecyl silane chemically bonded silica gel is used as filler, water-acetonitrile-methanol (15:15:70) as mobile phase, detective wavelength is 285 nm, flow rate is 0.8 ml/min, the theoretical plates number calculated for fulvestrant peak should be more than 3000.

Example 1

Fulvestrant Microsphere and Preparation Thereof

This example is about the composition of fulvestrant microsphere and the preparation method thereof.

Prescription:

| Oil Phase: | Fulvestrant | 0.5 g |
|---|---|---|
| | Methoxy ended polyethylene glycol-polylactic acid block copolymer | 5.0 g |
| | Dichloromethane | 50 ml |
| Water Phase: | 1.0% Polyvinyl alcohol + 0.1% Tween-80 solution | 3000 ml |

Note:
The weight average molecular weight (Mw) of methoxy ended polyethylene glycol-polylactic acid block copolymer is 2000/20000 and the structural formula of which is

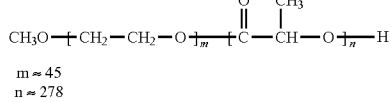

m ≈ 45
n ≈ 278

Preparation method: the in-liquid drying method is used. Fulvestrant and methoxy ended polyethylene glycol-polylactic acid block copolymer are added into dichloromethane and sonicated to dissolve. The resulting solution is slowly added to the water phase under 3000 rpm high speed shear, and further sheared for 3 min. The resulting mixture is then placed in 30° C. water bath and stirred for 2 hours with the stirring rate of 300 rpm, further heated to 35° C. and stirred for 0.5 hour, and then heated to 40° C. and stirred for 0.5 hour, followed by filtered with 150 μm sieve mesh (there is almost no microsphere that is greater than 150 μm on the sieve). The filtrate is collected and filtered with 10 μm sieve mesh (there is a few microspheres that are less than 10 μm in the filtrate). The microspheres are collected and washed with 500 ml of water for 5 times. The wet microspheres are dried at 40° C. to obtain the dry product of totally 4.05 g with the yield of about 73.6%.

Indications: mainly used for the treatment of breast cancer and can be injected subcutaneously.

Main ingredients: Fulvestrant, methoxy ended polyethylene glycol-polylactic acid block copolymer (Mw=2000/20000).

Range of particle size and shape of particle: 10~150 μm, mostly 20~30 μm.

Drug loading: Drug loading is 9.0%, which is determined by HPLC method.

Encapsulation efficiency: 72.9%.

Example 2

Fulvestrant Microsphere and Preparation Thereof

This example is about another composition of fulvestrant microsphere and preparation method thereof.

Prescription:

| Oil Phase: | Fulvestrant | 0.5 g |
| --- | --- | --- |
| | Methoxy ended polyethylene glycol-polylactic acid block copolymer | 5.0 g |
| | Dichloromethane | 50 ml |
| Water Phase: | 1.0% Polyvinyl alcohol + 0.1% Tween-80 solution | 750 ml |

Note:
The weight average molecular weight (Mw) of methoxy ended polyethylene glycol-polylactic acid block copolymer is 2000/40000 and the structural formula of which is

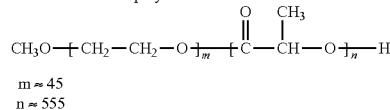

m ≈ 45
n ≈ 555

Preparation method: the in-liquid drying method is used. Fulvestrant and methoxy ended polyethylene glycol-polylactic acid block copolymer are added into dichloromethane and sonicated to dissolve. The resulting solution is slowly added to the water phase under 3000 rpm high speed shear, and further sheared for 3 min. The resulting mixture is then placed in 30° C. water bath and stirred for 2 hours with the stirring rate of 300 rpm, further heated to 35° C. and stirred for 0.5 hour, and then heated to 40° C. and stirred for 0.5 hour, followed by filtered with 150 μm sieve mesh (there is almost no microsphere that is greater than 150 μm on the sieve). The filtrate is collected and filtered with 10 μm sieve mesh (there are a few microspheres that are less than 10 μm in the filtrate). The microspheres are collected and washed with 500 ml of water for 5 times. The wet microspheres are dried at 40° C. to obtain the dry product of totally 4.41 g with the yield of about 80%.

Indications: mainly used for the treatment of breast cancer and can be injected subcutaneously.

Main ingredients: Fulvestrant, methoxy ended polyethylene glycol-polylactic acid block copolymer (Mw=2000/40000).

Range of particle size and shape of particle: 10~150 μm, mostly 20~30 μm; the shape of particle is round.

Drug loading: Drug loading is 11.0%, which is determined by HPLC method.

Encapsulation efficiency: 87.7%.

Example 3

Fulvestrant Microsphere and Preparation Thereof

This example is about another composition of fulvestrant microsphere and preparation method thereof.

Prescription:

| Oil Phase: | Fulvestrant | 0.5 g |
| --- | --- | --- |
| | Methoxy ended polyethylene glycol-polylactic acid block copolymer | 5.0 g |
| | Dichloromethane | 50 ml |
| Water Phase: | 0.5% Polyvinyl alcohol solution | 750 ml |

Note:
The weight average molecular weight (Mw) of methoxy ended polyethylene glycol-polylactic acid block copolymer is 2000/20000 and the structural formula of which is

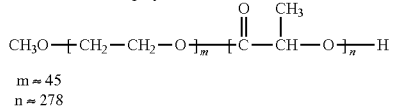

m ≈ 45
n ≈ 278

Preparation method: the in-liquid drying method is used. Fulvestrant and methoxy ended polyethylene glycol-polylactic acid block copolymer are added into dichloromethane and sonicated to dissolve. The resulting solution is slowly added to the water phase under 2800 rpm high speed shear, and further sheared for 5 min. The resulting mixture is then placed in 35° C. water bath and stirred for 4 hours with the stirring rate of 300 rpm, further heated to 40° C. and stirred for 0.5 hour, and then filtered with 150 μm sieve mesh. The filtrate is collected and filtered with 10 μm sieve mesh. The microspheres are collected and washed with 500 ml water for 5 times. The wet microspheres are dried at 40° C. to obtain the dry product of totally 5.07 g with the yield of about 92%.

Range of particle size and shape of particle: 10~150 μm, mostly 20~30 μm, and secondly 60~30 μm; the shape of particle is round.

Drug loading: Drug loading is 8.3%, which is determined by HPLC method.

Encapsulation efficiency: 84.2%.

Example 4

Study on Fulvestrant Microsphere Release In Vitro

This example studies on the fulvestrant microsphere release in vitro taking the fulvestrant microsphere prepared in Example 1 and 2 as the test sample.

1) Experimental Instrument and Reagents

Instrument: SHA-A Water-bathing Constant Temperature Vibrator, and High Performance Liquid Chromatograph obtained from JASCO, Inc., Japan (UV-2075 UV Detector, PU-2089 injection pump, AS-2055 Autosampler).

Test drug: Fulvestrant with the purity of 100.0%, which is obtained from Xi'an Libang Pharmaceutical Co., Ltd, China.

Reagents: acetonitrile and methanol, chromatographic grade, obtained from TEDIA Company, US; dichloromethane, analytically pure, obtained from Tianjin Kermel Chemical Reagent Co., Ltd. China; Tween-80, obtained from CRODA Company, Britain.

Test Samples: Fulvestrant sample 1 (fulvestrant microsphere prepared in Example 1), Fulvestrant sample 2 (fulvestrant microsphere prepared in Example 2), both are obtained from Xi'an Libang Pharmaceutical Co., Ltd.

Chromatographic conditions: The HPLC method is used. The octadecyl silane chemically bonded silica gel is used as filler, water-acetonitrile-methanol (15:15:70) as mobile phase with the detective wavelength of 285 nm, the flow rate of 0.8 ml/min, and the number of theoretical plates calculated for fulvestrant peak should be more than 3000.

2) Experimental Method:

6 samples that each has 25 mg of fulvestrant are accurately weighed respectively, and placed in 6 glass infusion bottles respectively. 50 ml of 0.3% Tween-80 solution preheated to 37° C. is accurately added to each of the glass infusion bottle. The glass infusion bottles are closed tightly with rubber stoppers and capped with aluminum caps, rapidly fixed in 37° C.±2° C. water bath at horizontal state, and shook immediately with the amplitude of about 4 cm at the horizontal direction and frequency of 100 times per minute. 1 ml of suspension is extracted from each of the bottle through rubber stopper at 1, 2, 4, 8, 24, 28, and 40 hours after shaking (if the contents in the suspension has precipitated, it should be extracted after shaking to uniform distribution), and then 1 ml of 0.3% Tween-80 solution is supplemented to each of the bottle. The suspension is filtered on 0.2 μm of filter membrane as the test sample solution. In addition, appropriate amount of fulvestrant is accurately weighed, to which dichloromethane is added to dissolve and dilute it to contain 2.0 mg fulvestrant per 1 ml solution. 1 ml of the solution is accurately taken and placed in 25 ml volumetric flask. The total volume is determined to 25 ml by adding acetonitrile. The solution is shook well, and used as the control solution. 20 μl of test solution and 20 μl control solution are accurately taken, and injected into the chromatograph. The chromatogram is recorded, and the cumulated release amount is calculated with peak area by external standard method.

3) Experimental Results and Conclusions

Figure 2:
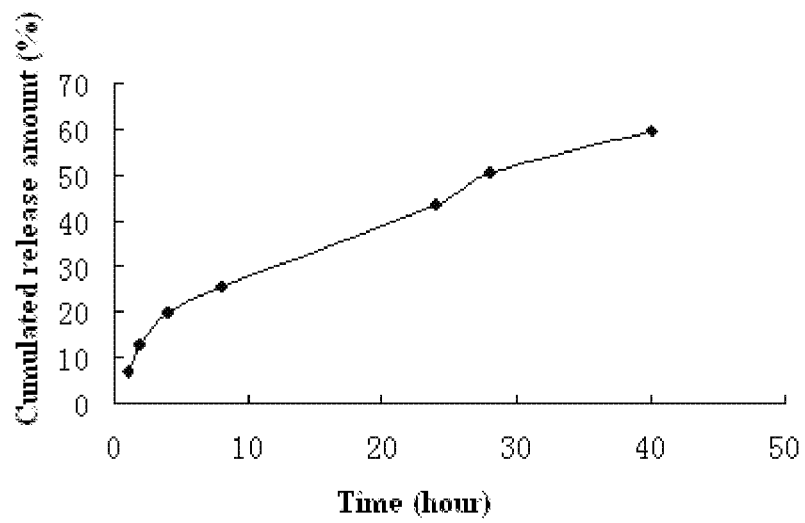
FIG. 2 is a release curve of fulvestrant microsphere sample 2 in vitro.

The results of drug release in vitro of two types of fulvestrant microsphere samples are presented in FIGS. 1 and 2. It can be seen from the results that the release rate of these two types of fulvestrant microsphere samples are stable and there is no burst effect, but the release rate of sample 1 is significantly higher than that of sample 2. It shows that the drug release rate in vitro is decreased with the increase of the molecular weight of the carrier material, suggesting that the release rate of fulvestrant microsphere can be adjusted by the size of molecular weight.

Example 5

Studies on the Pharmacokinetics of Fulvestrant Microsphere in Rat

This example studies on the pharmacokinetics of fulvestrant microsphere in rat taking the fulvestrant microspheres prepared in Example 1 and 2 as test sample.

1) Experimental Instrument and Reagents

Instrument: Micromass Quattro micro liquid chromatograph-mass spectrum (LC-MS), containing autosampler, column oven, electrospray ionization interface, 2695 liquid chromatograph and Masslynx 4.0 MS workstation; METTLER one hundred-thousandth of electronic balance; Milli-Q Water Purifior; MICROMAX 3591 Centrifuge Desk High Speed Centrifuge (Thermo Electron); Turbine mixer (Huxi analytical instrument factory, Shanghai, China).

Reagents: methanol, chromatographic grade, obtained from TEDIA Company, US; the remaining reagents are commercially available analytical pure; double distilled water, which is self prepared and purified by Milli-Q Water Purifior.

Test drug: The active pharmaceutical ingredient, fulvestrant: 99%.

Test Samples Fulvestrant microsphere sample 1 (fulvestrant microsphere prepared in Example 1) with the content of 9.0%; Fulvestrant microsphere sample 2 (fulvestrant microsphere prepared in Example 2) with the content of 11.0%.

Solvent of microsphere sample (Each 1 ml solvent of sample contains: 50 mg of mannitol, 5 mg of carboxymethylcellulose sodium, 1 mg of Tween-80 and appropriate amount of water for injection): 2 bottles with 50 ml/bottle.

All the above mentioned products are provided by Xi'an Libang Pharmaceutical Co., Ltd., China.

All the fulvestrant microsphere samples are prepared to 10 mg/ml using the solvent of microsphere sample.

Emodin: internal standard, provided by the National Institute for the Control of Pharmaceutical and Biological Products, China, Batch No.: 0756-200110; and used for the content determination.

HPLC conditions:

Mobile phase: Methanol: Water=85:15 (v:v);

Chromatographic column: 100×2.0 mm, shim-pack; pre-column phenomenex C18 (ODS Octadecyl), 4 mm×2.0 ID 10/pk; column temperature: 35° C.; injection volume: 5 μL; flow rate: 0.2 ml/min;

LC-MS-MS Conditions:

Capillary voltage: 3.00 kV; Cone voltage: 30 V; Extractor voltage: 3.00 V; RF Lens Voltage: 0.3 V; Source Temp: 120° C.; Desolvation Temp: 400° C.; Cone Gas Flow: 30 L/Hr;

Desolvation gas flow: 500 L/Hr; LM1 Resolution: 13.0; HM1 Resolution: 13.0; Ion Energy: 10.5; Entrance: −2; Collision: 20; Exit: 2; LM2 Resolution: 13.0; HM2 Resolution: 13.0;

Ion Energy: 10.5; Gas cell pirani pressure: 4.0e-3 millibar;

Fulvestrant: [M-H+] m/z 605.6→427.4;

Emodin: [M-H+] m/z 269.4→225.1.

2) Experimental Methods:

12 Sprague-Dawley rates (purchased from the Laboratory Animal Centre of Nantong University; Jiangsu, China) are all female with the body weight of 180~220 g. The SD rats are divided into two groups and each group has 6 rats, which are groups of samples 1 and 2. 50 mg/kg (i.e. 1 ml/200 g) of fulvestrant formulation with different prescription are administered subcutaneously to the rats. 0.3 ml blood is collected from the eye socket vein in a heparinized tube before administration and at 0.5, 1, 3, 6, 10, 24 hours, on Day 2, 4, 7, 10, 14, 21, 28 and Week 5, 6, 7, 8, 9, 10, 11, 12, 13 after administration respectively, centrifuged at 3500 rpm for 10 min. The blood plasma (0.1 ml) is collected quantificationally, and is ready for analysis.

3) Data Analysis:

The AUC, Tmax and Cmax as well as the other parameters are calculated using the data of plasma concentration-time in each animal. The results are shown in table 1.

TABLE 1

The pharmacokinetic parameters in rats after subcutaneous injection of fulvestrant microsphere

|  | AUC(0-∞) | t½z | Tmax | Cmax |
|---|---|---|---|---|
| Unit | Ng · mL−1 · h | h | h | Ng · mL−1 |
| Sample 1 | 2992.1 ± 1096.6 | 133.0 ± 53.3 | 120.6 ± 72.8 | 13.2 ± 6.1 |
| Sample 2 | 1824.2 ± 1659.7 | 511.8 ± 581.9 | 6.0 ± 0.0 | 8.1 ± 2.1 |

Figure 3:
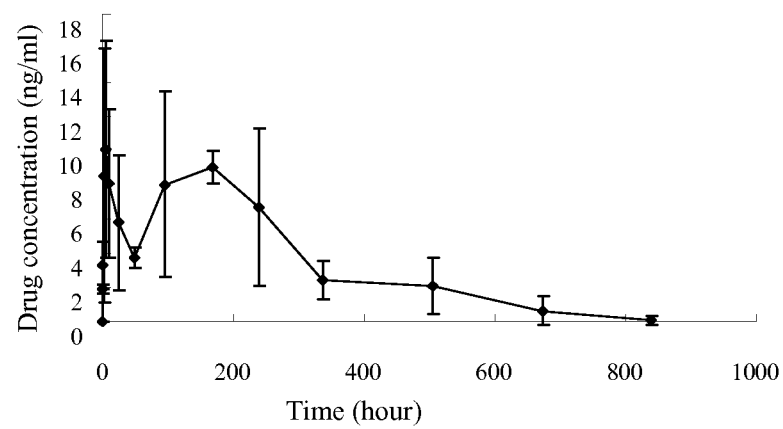
FIG. 3 is the mean drug plasma concentration-time curve in rats after subcutaneous administration of fulvestrant microsphere sample 1.
Figure 4:
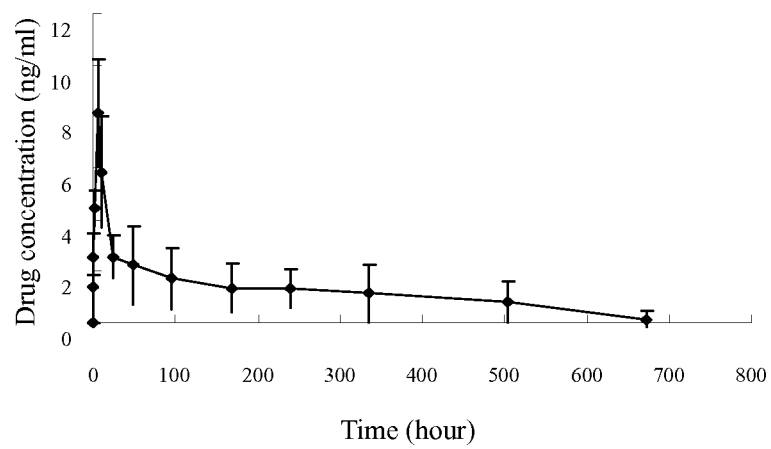
FIG. 4 is the mean drug plasma concentration-time curve in rats after subcutaneous administration of fulvestrant microsphere sample 2.

The mean drug plasma concentration-time curves in rats after subcutaneous injection of fulvestrant microsphere are presented in FIGS. 3 and 4. Furthermore, no irritant reaction is observed on the administration site upon pathological examination.

4) Analysis on Experimental Results:

The methoxy ended polyethylene glycol-polylactic acid block copolymer with the Mw of 2000~20000 is used as microsphere carrier material in sample 1, while the methoxy ended polyethylene glycol-polylactic acid block copolymer with the Mw of 2000~40000 is used as microsphere carrier material in sample 2. The experimental data shows that, as compared with sample 2, sample 1 has faster release rate, more release amount, shorter peak time, but has shorter half-life than sample 2, indicating that the release rate is slowed and the half-life is prolonged with the molecular weight increasing of fulvestrant microsphere, which is consistent with the results of drug release in vitro. Thus, the desired drug release curve may be obtained by regulation of the molecular weight size.

Furthermore, no irritant reaction is observed on the administration site upon pathological examination, indicating that fulvestrant microsphere has better biocompatibility.

Example 6

Study on the In Vitro Release of Fulvestrant Microsphere in Different Release Medium This example studies on the in vitro release of fulvestrant microsphere in different release medium taking the fulvestrant microsphere prepared in Example 3 as the test sample.

1) Experimental Instruments and Reagents

Instrument: SHA-A Water-bathing Constant Temperature Vibrator, and High Performance Liquid Chromatograph obtained from JASCO, Inc., Japan (UV-2075 UV Detector, PU-2089 injection pump, AS-2055 Autosampler).

Test drug: Fulvestrant with the purity of 100.0%, obtained from Xi'an Libang Pharmaceutical Co., Ltd., China.

Reagents: acetonitrile and methanol, chromatographic grade, obtained from TEDIA Company, US; dichloromethane, analytically pure, obtained from Tianjin Kermel Chemical Reagent Co., Ltd., China; Tween-80, obtained from CRODA Company, Britain.

Test Sample: Fulvestrant microsphere (fulvestrant microsphere prepared in Example 3), obtained from Xi'an Libang Pharmaceutical Co., Ltd, China.

Chromatographic conditions: The HPLC method is used. The octadecyl silane chemically bonded silica gel is used as filler, water-acetonitrile-methanol (15:15:70) as mobile phase with the detective wavelength of 285 nm, the flow rate of 0.8 ml/min, and the number of theoretical plates calculated for fulvestrant peak should be more than 3000.

3) Experimental Method 12 samples that each has 25 mg of fulvestrant microsphere are accurately weighed respectively, placed in 12 glass infusion bottles respectively and divided into four groups equally. 50 ml of release medium preheated to 37° C. is accurately added to each of the glass infusion bottle. The release medium is 0.3% of Tween-80 solution in group 1, 0.5% of Tween-80 solution in group 2, 0.05% of Cetyltrimethyl Ammonium Bromide (CTAB) solution in group 3 and 0.1% of Cetyltrimethyl Ammonium Bromide solution in group 4. The glass infusion bottles are closed tightly with rubber stoppers and capped with aluminum caps, then rapidly fixed in 37° C.±2° C. water bath at horizontal state, followed by shook immediately with the amplitude of about 4 cm at the horizontal direction and the frequency of 100 times per minute. 1 ml of suspension is extracted from each of the bottle through rubber stopper at 1, 2, 4, 20, 27 and 44 hours after shaking (if the contents in the suspension has precipitated, it should be extracted after shaking to uniform distribution), and then 1 ml corresponding release medium is supplemented to each of the bottle. The suspension is filtered on 0.2 μm of filter membrane as the test sample solution. In addition, appropriate amount of fulvestrant is accurately weighed, to which dichloromethane is added to dissolve and dilute it to contain 2.0 mg fulvestrant per 1 ml solution. 1 ml solution is accurately taken and placed in 25 ml volumetric flask. The total volume is determined to 25 ml by adding acetonitrile. The solution is shook well and used as the control solution. 20 μl of test solution and 20 μl of control solution are accurately taken and injected into the chromatograph. The chromatogram is recorded. The cumulated release amount is calculated with peak area by external standard method.

3) Experimental Results and Conclusions

Figure 5:
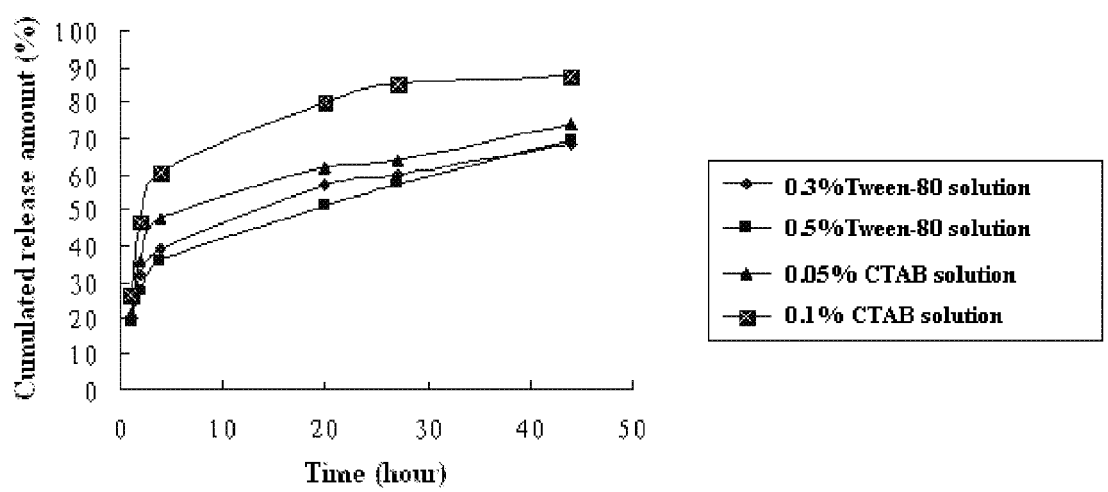
FIG. 5 is a drug release curve of fulvestrant microsphere in different release medium.

The result of fulvestrant microsphere release in different medium is shown in FIG. 5. It can be seen from the result that the release rate of fulvestrant microsphere samples in four groups of release mediums is stable and there is no burst effect. With the increasing of the concentration of surface active agent, the drug release rate is faster, but the increase of the drug release rate in Tween-80 group is less significant than Cetyltrimethyl Ammonium Bromide(CTAB) solution group.

Examples 7-9 are examples of using the solvent-nonsolvent method for preparing fulvestrant micro sphere Example 7

Using Solvent-Nonsolvent Method for Preparing Fulvestrant Microsphere-1

Prescription:

| Solvent Phase: | Fulvestrant | 0.05 g |
|---|---|---|
| | Methoxy ended polyethylene glycol-polylactic acid block copolymer | 1.0 g |
| | Trichloromethane | 10 ml |
| Nonsolvent Phase: | Polyisobutyl ester | 0.05 g |
| | Cyclohexane | 100 ml |

Note:
The weight average molecular weight (Mw) of methoxy ended polyethylene glycol-polylactic acid block copolymer is 5000/10000 and the structural formula of which is $$CH_3O\mathrm{-\!\!+\!\!}CH_2\mathrm{-\!}CH_2\mathrm{-\!}O\mathrm{\!\!+\!\!}_m\mathrm{-\!\!+\!\!}\overset{O}{\underset{\|}{C}}\mathrm{-\!}\overset{CH_3}{\underset{|}{CH}}\mathrm{-\!}O\mathrm{\!\!+\!\!}_n\mathrm{-\!}H$$

m ≈ 113
n ≈ 139

Preparation method: the solvent-nonsolvent method is used for preparation. The polyisobutyl ester is added to cyclohexane and sonicated to dissolve, and the resulting solution is used as nonsolvent phase and ready for use. Fulvestrant and methoxy ended polyethylene glycol-polylactic acid block copolymer are added to trichloromethane and sonicated to dissolve, and the resulting solution is used as solvent phase. The solvent phase is slowly added to the nonsolvent phase under 6000 rpm high speed shear, and further sheared for 5 min, and then stirred for 30 min with the stirring rate of 300 rpm, and filtered with 0.5 mm sieve mesh. The filtrate is collected and filtered with 20 μm sieve mesh. The microspheres are collected and dried at 40° C. for 2 hours to get the fulvestrant microspheres.

Range of particle size and shape of particle: 20 μm~1 mm, mostly 50~200 μm; the shape of particle is round.

Drug loading: Drug loading is 4.6%, which is determined by HPLC method.

Encapsulation efficiency: 67.6%.

Example 8

Using Solvent-Nonsolvent Method for Preparing Fulvestrant Microsphere-2

Prescription:

| Solvent Phase: | Fulvestrant | 0.2 g |
|---|---|---|
| | Methoxy ended polyethylene glycol-polylactic acid block copolymer | 1.0 g |
| | Span-85 | 0.05 g |
| | Dichloromethane | 10 ml |
| | Silicone oil | 30 ml |
| Nonsolvent Phase: | Petroleum ether | q.s. |

Note:
The weight average molecular weight (Mw) of methoxy ended polyethylene glycol-polylactic acid block copolymer is 2000/20000 and the structural formula of which is

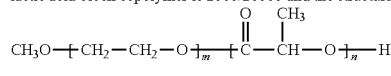

m ≈ 45
n ≈ 278

Preparation method: the solvent-nonsolvent method is used for preparation. Fulvestrant, methoxy ended polyethylene glycol-polylactic acid block copolymer and Span-85 are added into dichloromethane and sonicated to dissolve, then added to the silicone oil under the stirring rate of 600 rpm, and stirred to emulsify. The petroleum ether is slowly added to the solution until the microspheres are no longer produced. Then the solution is stirred for 30 min with the stirring rate of 300 rpm, and filtered with 1 mm sieve mesh. The filtrate is collected and filtered with 20 μm sieve mesh. The microspheres are collected, washed with 100 ml water for 5 times and dried at 40° C. for 2 hours to get the fulvestrant microspheres.

Range of particle size and shape of particle: 20 μm~1 mm, mostly 50~500 μm; the shape of particle is round.

Drug loading: Drug loading is 16.8%, which is determined by HPLC method.

Encapsulation efficiency: 65.5%.

Example 9

Using Solvent-Nonsolvent Method for Preparing Fulvestrant Microsphere-3

Prescription:

| Solvent Phase: | Fulvestrant | 0.5 g |
|---|---|---|
| | Methoxy ended polyethylene glycol-polylactic acid block copolymer | 1.0 g |
| | Span-85 | 0.05 g |
| | Dichloromethane | 20 ml |
| | Liquid paraffin | 50 ml |
| Nonsolvent Phase: | Pure water | q.s. |

Note:
The weight average molecular weight (Mw) of methoxy ended polyethylene glycol-polylactic acid block copolymer is 2000/40000 and the structural formula of which is

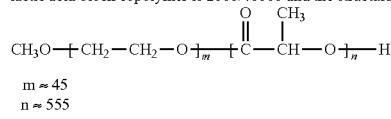

m ≈ 45
n ≈ 555

Preparation method: the solvent-nonsolvent method is used for preparation. Fulvestrant, methoxy ended polyethylene glycol-polylactic acid block copolymer and Span-85 are added into dichloromethane and sonicated to dissolve, then added to the liquid paraffin under the stirring rate of 3000 rpm, and stirred to emulsify. The pure water is slowly added to the solution under the stirring rate of 300 rpm until the microspheres are no longer produced. Then the solution is stirred for 30 min and filtered with 600 μm sieve mesh. The filtrate is collected and filtered with 10 μm sieve mesh. The microspheres are collected, washed with 100 ml water for 5 times and dried at 40° C. for 2 hours to get the fulvestrant microspheres.

Range of particle size and shape of particle: 10 μm~600 μm, mostly 40~250 μm; the shape of particle is round.

Drug loading: Drug loading is 46.1%, which is determined by HPLC method.

Encapsulation efficiency: 78.8%.

Examples 10~14 are examples of using the in-liquid drying method for preparing fulvestrant microsphere

Example 10

Using in-Liquid Drying Method for Preparing Fulvestrant Microsphere-1

Prescription:

| Oil Phase: | Fulvestrant | 0.05 g |
|---|---|---|
| | Methoxy ended polyethylene glycol-polylactic acid block copolymer | 0.5 g |
| | Dichloromethane | 5 ml |
| Water Phase: | 1.0% Polyvinyl alcohol + 0.1% Tween-80 solution | 100 ml |

Note:
The weight average molecular weight (Mw) of methoxy ended polyethylene glycol-polylactic acid block copolymer is 5000/10000 and the structural formula of which is

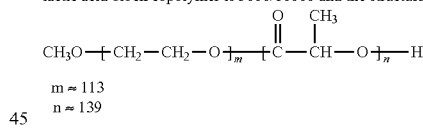

m ≈ 113
n ≈ 139

Preparation method: the in-liquid drying method is used. Fulvestrant and methoxy ended polyethylene glycol-polylactic acid block copolymer are added into dichloromethane and sonicated to dissolve. The resulting solution is slowly added to the water phase under 5000 rpm high speed shear, and further sheared for 3 min. The resulting mixture is then placed in 30° C. water bath and stirred for 2 hours with the stirring rate of 300 rpm, further heated to 35° C. and stirred for 0.5 hour, and then heated to 40° C. and stirred for 0.5 hour, followed by filtered with 150 μm sieve mesh. The filtrate is collected and filtered with 10 μm sieve mesh. The microspheres are collected and washed with 100 ml water for 5 times. The wet microspheres are dried at 40° C. to obtain the fulvestrant microspheres.

Range of particle size and shape of particle: 10~150 μm, mostly 20~30 μm; the shape of particle is round.

Drug loading: Drug loading is 9.1%, which is determined by HPLC method.

Encapsulation efficiency: 64.5%.

Example 11

Using in-Liquid Drying Method for Preparing Fulvestrant Microsphere-2

Prescription:

| Oil Phase: | Fulvestrant | 0.05 g |
|---|---|---|
| | Methoxy ended polyethylene glycol-polylactic acid block copolymer | 0.5 g |
| | Dichloromethane | 5 ml |
| Water Phase: | 1.0% Polyvinyl alcohol + 0.1% Tween-80 solution | 300 ml |

Note:
The weight average molecular weight (Mw) of methoxy ended polyethylene glycol-polylactic acid block copolymer is 2000/20000 and the structural formula of which is

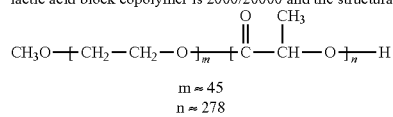

$m \approx 45$
$n \approx 278$

Preparation method: the in-liquid drying method is used. Fulvestrant and methoxy ended polyethylene glycol-polylactic acid block copolymer are added into dichloromethane and sonicated to dissolve. The resulting solution is slowly added to the water phase under 3000 rpm high speed shear, and further sheared for 3 min. The resulting mixture is then placed in 30° C. water bath and stirred for 2 hours with the stirring rate of 300 rpm, further heated to 35° C. and stirred for 0.5 hour, and then heated to 40° C. and stirred for 0.5 hour, followed by filtered with 150 μm sieve mesh. The filtrate is collected and filtered with 10 μm sieve mesh. The microspheres are collected and washed with 200 ml water for 5 times. The wet microspheres are dried at 40° C. to obtain the fulvestrant microspheres.

Range of particle size and shape of particle: 10~150 μm, mostly 20~50 μm; the shape of particle is round.
Drug loading: Drug loading is 9.5%, which is determined by HPLC method.
Encapsulation efficiency: 68.0%.

Example 12

Using in-Liquid Drying Method for Preparing Fulvestrant Microsphere-3

Prescription:

| Oil Phase: | Fulvestrant | 0.1 g |
|---|---|---|
| | Methoxy ended polyethylene glycol-polylactic acid block copolymer | 0.5 g |
| | Dichloromethane | 5 ml |
| Water Phase: | 0.1% Hydroxypropyl methylcellulose (HPMC) | 75 ml |

Note:
The weight average molecular weight (Mw) of methoxy ended polyethylene glycol-polylactic acid block copolymer is 2000/40000 and the structural formula of which is

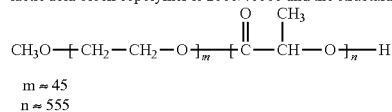

$m \approx 45$
$n \approx 555$

Preparation method: the in-liquid drying method is used. Fulvestrant and methoxy ended polyethylene glycol-polylactic acid block copolymer are added to dichloromethane and sonicated to dissolve. The resulting solution is slowly added to the water phase under 3000 rpm high speed shear, and further sheared for 3 min. The resulting mixture is then placed in 30° C. water bath and stirred for 3 hours with the stirring rate of 300 rpm, further heated to 40° C. and stirred for 1 hour, followed by filtered with 150 μm sieve mesh. The filtrate is collected and filtered with 10 μm sieve mesh. The microspheres are collected and washed with 200 ml water for 5 times. The wet microspheres are lyophilized (The pre-frozen temperature is −45° C., and the primary drying temperature is 25° C.) to obtain the fulvestrant microspheres.

Range of particle size and shape of particle: 10~150 μm, mostly 20~50 μm; the shape of particle is round.
Drug loading: Drug loading is 16.5%, which is determined by HPLC method.
Encapsulation efficiency: 69.7%.

Example 13

Using in-Liquid Drying Method for Preparing Fulvestrant Microsphere-4

Prescription:

| Oil Phase: | Fulvestrant | 0.2 g |
|---|---|---|
| | Methoxy ended polyethylene glycol-polylactic acid block copolymer | 2.0 g |
| | Dichloromethane | 20 ml |
| Water Phase: | 20% glycerol, 0.2% Tween-80 solution | 300 ml |

Note:
The weight average molecular weight (Mw) of methoxy ended polyethylene glycol-polylactic acid block copolymer is 2000/20000 and the structural formula of which is

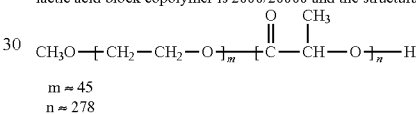

$m \approx 45$
$n \approx 278$

Preparation method: the in-liquid drying method is used. Fulvestrant and methoxy ended polyethylene glycol-polylactic acid block copolymer are added to dichloromethane and sonicated to dissolve. The resulting solution is slowly added to the water phase under 3000 rpm high speed shear, and further sheared for 3 min, and then homogenized with high pressure homogenizer for 3 times at the pressure of 800 bar and the room temperature. The emulsion is placed in 35° C. water bath and stirred for 2 hours with the stirring rate of 300 rpm, further heated to 40° C. and stirred for 1 hour, followed by filtered with 1 μm sieve mesh. The filtrate is collected and filtered with 0.1 μm sieve mesh. The microspheres are collected and washed with 100 ml water for 5 times. The wet microspheres are lyophilized (The pre-frozen temperature is −45° C., and the primary drying temperature is 25° C.) to obtain the fulvestrant microspheres.

Range of particle size and shape of particle: 0.1~1 μm, mostly 0.5~0.8 μm; the shape of particle is round.
Drug loading: Drug loading is 8.5%, which is determined by HPLC method.
Encapsulation efficiency: 56.5%.

Example 14

Using in-Liquid Drying Method for Preparing Fulvestrant Microsphere-5

Prescription:

| Oil Phase: | Fulvestrant | 0.1 g |
|---|---|---|
| | Methoxy ended polyethylene glycol-polylactic acid block copolymer | 1.0 g |

-continued

| | |
|---|---|
| Dichloromethane | 10 ml |
| Water Phase: 0.05 mol/L borax solution (containing 0.1% HPMC) | 200 ml |

Note:
The weight average molecular weight (Mw) of methoxy ended polyethylene glycol-polylactic acid block copolymer is 2000/40000 and the structural formula of which is

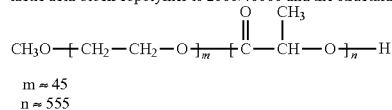

m ≈ 45
n ≈ 555

Preparation method: the in-liquid drying method is used. Fulvestrant and methoxy ended polyethylene glycol-polylactic acid block copolymer are added to dichloromethane and sonicated to dissolve. The resulting solution is slowly added to the water phase under 3000 rpm high speed shear, and further sheared for 3 min, and then emulsified with minitype jet pump for 5 times at the pressure of 500 bar and the room temperature. The emulsion is placed in 35° C. water bath and stirred for 2 hours with the stirring rate of 300 rpm, further heated to 40° C. and stirred for 1 hour, followed by filtered with 1 μm sieve mesh. The filtrate is collected and filtered with 0.1 μm sieve mesh. The microspheres are collected and washed with 100 ml of water for 5 times. The wet microspheres are lyophilized (The pre-frozen temperature is −45° C., and the primary drying temperature is 25° C.) to obtain the fulvestrant microspheres.

Range of particle size and shape of particle: 0.1~1 μm, mostly 0.3~0.7 μm; the shape of particle is round.
Drug loading: Drug loading is 9.1%, which is determined by HPLC method.
Encapsulation efficiency: 60.0%.

Examples 15~17 are the examples of using spray drying method for preparing fulvestrant micro sphere

Example 15

Using Spray Drying Method for Preparing Fulvestrant Microsphere-1

Prescription:

| | |
|---|---|
| Fulvestrant | 0.2 g |
| Methoxy ended polyethylene glycol-polylactic acid block copolymer | 2.0 g |
| Glycerol monostearates | 0.05 g |
| Tetrahydrofran | 50 ml |

Note:
The weight average molecular weight (Mw) of methoxy ended polyethylene glycol-polylactic acid block copolymer is 5000/10000 and the structural formula of which is

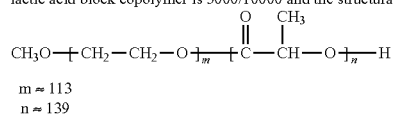

m ≈ 113
n ≈ 139

Preparation method: The methoxy ended polyethylene glycol-polylactic acid block copolymer is added to tetrahydrofran and sonicated to dissolve, then the glycerol monostearate and fulvestrant are added and sonicated to dissolve, and followed by spray drying with the ring fan blowing rate of 90%, the pressure is regulated to maximum, the inlet air temperature of 80° C. and the feed speed of peristaltic pump of 10%. After finishing drying, the resulting product is sieved, and then 10~300 μm of microspheres are collected to produce the fulvestrant microspheres.

Range of particle size and shape of particle: 10 μm~300 μm, mostly 50~150 μm; the shape of particle is round.
Drug loading: Drug loading is 9.9%, which is determined by HPLC method.
Encapsulation efficiency: 67.7%.

Example 16

Using Spray Drying Method for Preparing Fulvestrant Microsphere-2

Prescription:

| | |
|---|---|
| Fulvestrant | 0.6 g |
| Methoxy ended polyethylene glycol-polylactic acid block copolymer | 3.0 g |
| Cholesterol | 0.1 g |
| Dibutyl sebacate | 0.15 g |
| Dichloromethane | 30 ml |

Note:
The weight average molecular weight (Mw) of methoxy ended polyethylene glycol-polylactic acid block copolymer is 2000/20000 and the structural formula of which is

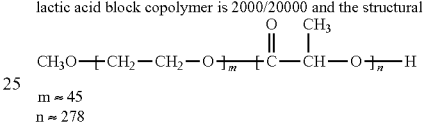

m ≈ 45
n ≈ 278

Preparation method: The methoxy ended polyethylene glycol-polylactic acid block copolymer is added to dichloromethane and stirred to dissolve, then the dibutyl sebacate, cholesterol and fulvestrant are added in turn and stirred to dissolve, and followed by spray drying with the ring fan blowing rate of 90%, the pressure is regulated to maximum, the inlet air temperature of 40° C. and the feed speed of peristaltic pump of 10%. After finishing drying, the resulting product is sieved, and then 10~300 μm of microspheres are collected to produce the fulvestrant microspheres.

Range of particle size and shape of particle: 10 μm~300 μm, mostly 50~150 μm; the shape of particle is round.
Drug loading: Drug loading is 19.4%, which is determined by HPLC method.
Encapsulation efficiency: 62.1%.

Example 17

Using Spray Drying Method for Preparing Fulvestrant Microsphere-3

Prescription:

| | |
|---|---|
| Fulvestrant | 1.0 g |
| Methoxy ended polyethylene glycol-polylactic acid block copolymer | 2.0 g |
| Dichloromethane | 40 ml |

Note:
The weight average molecular weight (Mw) of methoxy ended polyethylene glycol-polylactic acid block copolymer is 2000/40000 and the structural formula of which is

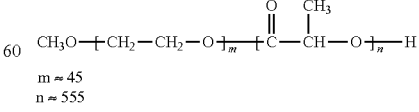

m ≈ 45
n ≈ 555

Preparation method: Fulvestrant and methoxy ended polyethylene glycol-polylactic acid block copolymer are added to dichloromethane and sonicated to dissolve, then spray dried with the ring fan blowing rate of 90%, the pressure is regulated to maximum, the inlet air temperature of 40° C. and the feed speed of peristaltic pump of 10%. After finishing drying, the resulting product is sieved, and then 10300 μm of microspheres are collected to get the fulvestrant microspheres.

Range of particle size and shape of particle: 10~300 μm, mostly 80~150 μm; the shape of particle is round.

Drug loading: Drug loading is 48.7%, which is determined by HPLC method.

Encapsulation efficiency: 56.5%.

What is claimed is:

1. A method of preparing fulvestrant microsphere, wherein the fulvestrant microsphere comprises:
   1) fulvestrant or pharmaceutically acceptable salt or solvate thereof and
   2) a methoxy ended polyethylene glycol-polylactic acid block copolymer,
   wherein the particle size of the fulvestrant microsphere is between 10 μm and 1 mm, the fulvestrant microsphere comprises between 16.5% and 50% weight of fulvestrant or pharmaceutically acceptable salt or solvate thereof based on the amount of fulvestrant; and
   wherein the method is spray drying method.

2. The method of claim 1, wherein the fulvestrant microsphere comprises between 20% and 30% weight of fulvestrant or pharmaceutically acceptable salt or solvate thereof based on the amount of fulvestrant.

3. The method of claim 1, wherein the methoxy ended polyethylene glycol-polylactic acid block copolymer is composed of hydrophilic fragment polyethylene glycol and lipophilic fragment polylactic acid.

4. The method of claim 1, wherein the particle size of the fulvestrant microsphere is 10~500 μm.

5. The method according to claim 1, wherein the spray drying method includes the steps of:
   a. dissolving or dispersing the fulvestrant in the solvent system containing dissolved methoxy ended polyethylene glycol-polylactic acid block copolymer;
   b. spraying into the drying tower of spray drying equipments in the form of spray, and drying, isolating, collecting.

6. The method of claim 3, wherein the structural formula of the methoxy ended polyethylene glycol-polylactic acid block copolymer is

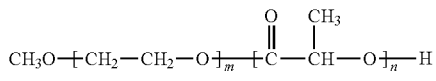

wherein: m = 4~454, n = 4~2778.

7. The method of claim 6, wherein m=11~227, n=70~2083.

8. The method of claim 6, wherein m=22~113, n=139~1111.

9. The method of claim 3, wherein the value of hydrophile-lipophile balance (HLB) of the methoxy ended polyethylene glycol-polylactic acid block copolymer is between 0.01 and 19.84.

10. The method of claim 9, wherein the HLB value is between 0.4 and 12.0.

11. The method of claim 9, wherein the HLB value is between 1.47 and 15.0.

12. The method of claim 5, wherein the solvent of the methoxy ended polyethylene glycol-polylactic acid block copolymer is one or more of dichloromethane, trichloromethane, methylhydrofuran, ethanol, and ethyl acetate.

13. The method of claim 5, wherein the concentration of the methoxy ended polyethylene glycol-polylactic acid block copolymer in the solvent system is 0.1%~50% (g/ml).

14. The method of claim 5, wherein the concentration of the dissolved or dispersed fulvestrant in the solvent system containing solved methoxy ended polyethylene glycol-polylactic acid block copolymer is 0.01%~50% (g/ml).

15. The method of claim 5, wherein the inlet air temperature of the drying tower is 30° C.~80° C.

16. The method of claim 5, wherein the solvent system further comprises a plasticizer, an antisticking agent or both.

17. The method of claim 16, wherein the plasticizer is one or more of dimethyl benzoate, diethyl benzoate, dibutyl benzoate, dibutyl sebacate, tributyl citrate, acetyl tributyl citrate, and glyceryl triacetate.

18. The method of claim 16, wherein the mass percent of the plasticizer to the methoxy ended polyethylene glycol-polylactic acid block copolymer is 0%~50%.

19. The method of claim 16, wherein the antisticking agent is one or more of cholesterol, glycerol monostearate, talc powder, silica gel, and magnesium stearateand.

20. The method of claim 16, wherein the mass percent of the antisticking agent to the methoxy ended polyethylene glycol-polylactic acid block copolymer is 0%~100%.

* * * * *